(12) United States Patent
Quan et al.

(10) Patent No.: US 9,168,200 B2
(45) Date of Patent: Oct. 27, 2015

(54) MICRONEEDLE PATCH CONTAINER

(71) Applicant: COSMED PHARMACEUTICAL CO., LTD., Kyoto, Kyoto (JP)

(72) Inventors: Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 14/345,567

(22) PCT Filed: Sep. 20, 2012

(86) PCT No.: PCT/JP2012/074048
§ 371 (c)(1),
(2) Date: Mar. 18, 2014

(87) PCT Pub. No.: WO2013/042723
PCT Pub. Date: Mar. 28, 2013

(65) Prior Publication Data
US 2014/0339117 A1 Nov. 20, 2014

(30) Foreign Application Priority Data
Sep. 22, 2011 (JP) ................................. 2011-225328

(51) Int. Cl.
*A61J 1/00* (2006.01)
*A61M 37/00* (2006.01)

(52) U.S. Cl.
CPC .............. *A61J 1/00* (2013.01); *A61M 37/0015* (2013.01); *A61M 2037/0023* (2013.01)

(58) Field of Classification Search
CPC ................ A61J 1/00; A61M 37/0015; A61M 2037/0023; A61B 19/026
USPC .................. 206/363–370, 438, 439, 570–572
See application file for complete search history.

(56) References Cited

U.S. PATENT DOCUMENTS 5,950,830 A 9/1999 Trigger
6,334,856 B1 1/2002 Allen et al.
(Continued)

FOREIGN PATENT DOCUMENTS

CN 101208129 A 6/2008
EP 2 062 611 A1 5/2009
(Continued)

OTHER PUBLICATIONS

Written Opinion of the International Searching Authority (PCT/ISA/237) for Application No. PCT/JP2012/074048 mailed Dec. 18, 2012 (English Translation mailed Apr. 3, 2014).
(Continued)

*Primary Examiner* — Bryon Gehman
(74) *Attorney, Agent, or Firm* — Cheng Law Group, PLLC (57) ABSTRACT

The present invention provides a microneedle patch container for effectively and hygienically securing a microneedle patch from manufacture to use. The container has a bottom surface recessed from the peripheral portion towards the center, a side surface connected to the bottom surface and the peripheral portion, and a bottom-surface protruding portion protruding from the bottom surface. The flexible release-type sheet portion of the microneedle patch is secured to the protruding portion on the bottom surface. A lid can also be used which has a recessed portion pressing against the microneedle patch secured to the bottom-surface protruding portion of the container in the position corresponding to the bottom-surface protruding portion. This is preferably housed inside a pouch molded from sterilized paper or sterilized film in order to keep the microneedle patch in an aseptic state.

11 Claims, 5 Drawing Sheets

(56) References Cited

U.S. PATENT DOCUMENTS

| | | |
|---|---|---|
| 6,503,231 B1 | 1/2003 | Prausnitz et al. |
| 6,611,707 B1 | 8/2003 | Prausnitz et al. |
| 6,622,864 B1 * | 9/2003 | Debbs et al. ............ 206/438 |
| 6,743,211 B1 | 6/2004 | Prausnitz et al. |
| 7,344,499 B1 | 3/2008 | Prausnitz et al. |
| 8,366,677 B2 * | 2/2013 | Kaspar et al. ............ 604/173 |
| 8,561,795 B2 * | 10/2013 | Schott ..................... 206/439 |
| 8,567,602 B2 * | 10/2013 | Niederberger et al. .... 206/363 |
| 2002/0022798 A1 | 2/2002 | Connelly et al. |
| 2002/0091357 A1 | 7/2002 | Trautman et al. |
| 2002/0138049 A1 | 9/2002 | Allen et al. |
| 2003/0208167 A1 | 11/2003 | Prausnitz et al. |
| 2004/0162518 A1 | 8/2004 | Connelly et al. |
| 2005/0137531 A1 | 6/2005 | Prausnitz et al. |
| 2005/0148926 A1 | 7/2005 | Trautman et al. |
| 2006/0257386 A1 | 11/2006 | Zimmerman et al. |
| 2006/0257509 A1 | 11/2006 | Zimmerman et al. |
| 2007/0083151 A1 | 4/2007 | Carter |
| 2007/0225676 A1 | 9/2007 | Prausnitz et al. |
| 2007/0254021 A1 | 11/2007 | Scimeca et al. |
| 2008/0200883 A1 | 8/2008 | Tomono |
| 2008/0208134 A1 | 8/2008 | Tomono |
| 2009/0131905 A1 | 5/2009 | Allen et al. |
| 2009/0292254 A1 | 11/2009 | Tomono |
| 2009/0292255 A1 | 11/2009 | Tomono |
| 2010/0228203 A1 | 9/2010 | Quan et al. |
| 2010/0256568 A1 | 10/2010 | Frederickson et al. |
| 2010/0285080 A1 | 11/2010 | Scimeca et al. |
| 2010/0312191 A1 | 12/2010 | Allen et al. |
| 2011/0127188 A1 * | 6/2011 | Thompson et al. ........ 206/438 |
| 2014/0186433 A1 | 7/2014 | Scimeca et al. |

FOREIGN PATENT DOCUMENTS

| | | |
|---|---|---|
| JP | 60-6334 A | 1/1985 |
| JP | 60-63344 U | 5/1985 |
| JP | 10-304934 A | 11/1998 |
| JP | 10-511330 A | 11/1998 |
| JP | 2002-517300 A | 6/2002 |
| JP | 2003-238347 A | 8/2003 |
| JP | 2004-506491 A | 3/2004 |
| JP | 2004-510534 A | 4/2004 |
| JP | 2006-56543 A | 3/2006 |
| JP | 2006-69633 A | 3/2006 |
| JP | 2006-346126 A | 12/2006 |
| JP | 2007-516781 A | 6/2007 |
| JP | 2008-518042 A | 5/2008 |
| JP | 2008-284318 A | 11/2008 |
| JP | 2008-543528 A | 12/2008 |
| JP | 3152532 U | 8/2009 |
| JP | 2010-29512 A | 2/2010 |
| JP | 2010-75485 A | 4/2010 |
| JP | 2010-75486 A | 4/2010 |
| WO | WO-99/64580 A1 | 12/1999 |
| WO | WO-00/74763 A2 | 12/2000 |
| WO | WO-01/92117 A2 | 12/2001 |
| WO | WO-2005/034891 A2 | 4/2005 |
| WO | WO-2006/041526 A1 | 4/2006 |
| WO | WO-2008/020633 A1 | 2/2008 |

OTHER PUBLICATIONS

International Search Report for the Application No. PCT/JP2012/074048 mailed Dec. 16, 2012.
Written Opinion of the International Searching Authority (PCT/ISA/237) for Application No. PCT/JP2012/074048 mailed Dec. 18, 2012.
Quan, Ving-Shu et al., "The Course of Development and Manufacturing for Microneedle, Yakuzaigaku", The Academy of Pharmaceutical Science and Technology, 2009, vol. 69, No. 4, pp. 272-276.
The First Office Action for the Application No, 201280044606.3 from The State Intellectual Property Office of the People's Republic of China dated Apr. 3, 2015.
Supplementary European Search Report for the Application No. EP 12 83 4191 dated Jul. 16, 2015.

* cited by examiner

MICRONEEDLE PATCH CONTAINER

TECHNICAL FIELD

The present invention relates to a container containing microneedle patches.

BACKGROUND ART

In order to impart modification effects and functional effects to a skin surface layer and a skin stratum corneum, liquid materials, ointments, cream preparations, tape preparations, patch preparations, poultice preparations, and the like containing medicinal ingredients have been conventionally used. Such preparations are intended to exhibit the effects by allowing the medicinal ingredients to penetrate into skin through their application or attachment to a skin surface. However, the above-mentioned conventional preparations cannot achieve sufficient effect, because simply applying the preparations to the skin brings about easy disappearance and loss of the medicinal ingredients due to a perspiration function of the skin, contact of the skin with the outside, and the like. Moreover, since the skin has a barrier function for preventing entry of foreign matters into a body, it is difficult to allow the medicinal ingredients to penetrate into the skin only through their application or attachment.

Recently, as a method for solving these drawbacks and surely supplying the medicinal ingredients into the skin, microneedles have been developed, and research thereof has been conducted. The microneedles are microscopic needles with a length of less than 1 mm (Patent Document 1). When the microneedles are made of material which is easily dissolved to disappear in vivo, the inserted microneedles are dissolved in the skin and then absorbed to disappear (Patent Document 2). Therefore, if the medicinal ingredients are contained in the microneedles beforehand, the medicinal ingredients can be supplied to a particular place in the skin. A microneedle array is formed by arranging a number of such microneedles on a substrate, and it has been largely expected on practical uses because a delivery amount can be increased in proportion to the number of the needles (Patent Documents 2 to 4, Non-patent Document 1). A microneedle patch is an easily usable product formed by supplementing the microneedle array with an adhesive tape and the like for sticking the microneedle array on the skin.

Because the microneedles have generally a length of shorter than 1 mm and a diameter of around 0.1 mm, they do not cause pain and bleeding at their insertion. An insert point closes quickly and does not leave any trace. As a result, the microneedles are recognized as an excellent method for delivering the particular medicinal ingredients to the particular point of the skin. The microneedles have attracted attention by having application as cosmetics, for example delivery of skin active components such as hyaluronic acid to the skin surface, concealment of lentigines and birthmarks, and the like, in addition to medical application such as delivery of vaccine.

An early microneedle comprised around 100 microneedles on a solid substrate with an area of around 1 cm$^2$. However, based on a recent increased demand for improving a wide part of a face at a time, a microneedle array comprising the microneedles on a softened substrate have been developed in order to fit the array to a non-planar face.

Suitable containers are necessary for providing the microneedle arrays to consumers in the market. Since the microneedle array has a needle portion and it is necessary to protect the needle portion during transport, sale or preservation, containers for patches, such as tapes, which are widely used conventionally (Patent Documents 5 and 6), cannot be used as they are. In addition, containers for solid substrates (Patent Documents 7 to 9) cannot be used for the microneedle array with a soft substrate.

CITATION LIST

Patent Documents

[Patent Document 1] JP 2002-517300 W
[Patent Document 2] JP 2003-238347 A
[Patent Document 3] JP 2006-346126 A
[Patent Document 4] JP 2008-284318 A
[Patent Document 5] JP 2006-056543 A
[Patent Document 6] JP 2008-518042 W
[Patent Document 7] Japanese Registered Utility Model No. 3152532
[Patent Document 8] JP 2010-75485 A
[Patent Document 9] JP 2010-75486 A

Non-Patent Document

[Non-patent Document 1] Quan Ying-Shu, Kamiyama Fumio, The Course of Development and Manufacturing for Microneedle, Yakuzaia; The Academy of Pharmaceutical Science and Technology. Japan; H21-Jul. 69(4), 272-276. 276.

SUMMARY OF INVENTION

Technical Problem

Since the microneedle patch is attached on skin to deliver the medicinal ingredients, it is necessary for the microneedle patch to be held hygienically so as not to lose its pharmacologic effect, during a period from its manufacture to use through a distribution process. For this purpose, the present invention aims to provide a microneedle patch container suitable for holding the microneedle patch in which an adhesive tape is supplemented to the microneedle array with the flexible substrate and a release sheet is attached on an adhesive surface of the tape.

Solution to Problem

In order to solve the above-mentioned problem, a microneedle patch container according to the present invention comprises: one or plural bottom surfaces recessed from a peripheral portion; a side surface continuously connecting the bottom surfaces with the peripheral portion; and a bottom-surface protruding portion projecting from the bottom surfaces, characterized in that a release sheet portion of a flexible microneedle patch is held with the bottom-surface protruding portion.

One microneedle patch container can contain the microneedle patches by the number of bottom surfaces. Generally, one microneedle patch container contains one microneedle patch. However, for example, in the case of the microneedle patch for being attached under an eye, since the microneedle patches are generally attached under right and left eyes, it is preferable in business to contain a set of two pieces. Moreover, two or more microneedle arrays may be held on one microneedle patch. In this case, two or more microneedle arrays can be contained in one container.

Preferably, the microneedle patch container according to the present invention is structured to comprise a lid, the lid having recessed portions which press the microneedle patch held on the bottom-surface protruding portion in a position corresponding to a part of the bottom-surface protruding portion, and the lid not having recessed portions in a position corresponding to other part of the bottom-surface protruding portion. Although the release sheet portion of the microneedle patch is held on the bottom-surface protruding portion, when the recessed portions of the lid are configured to press the entire release sheet portion, the microneedle patch is closely contacted to the lid by the effect of static electricity. If the microneedle patch is attracted to the lid by the static electricity, the microneedle patch is popped up suddenly when the lid is removed, and the microneedle patch is attracted to the container and thus hardly taken out. The press by the recessed portions of the lid is preferably partial to weaken influence of the static electricity and facilitate handling of the container. To further reduce the influence of the static electricity and prevent the microneedle patch from being attracted to the lid, it is efficient and desirable that an area of the bottom-surface protruding portion is made larger than an area of the recessed portions of the lid.

The bottom-surface protruding portion is preferably a nearly rectangular shape so as to easily press and hold the release sheet of the microneedles. Moreover, this rectangular shape may be divided into several parts so as to hold the four sides of the release sheet by a plurality of convex parts.

The microneedle patch container may be desirably stacked by fitting the plurality of container each other. To do so, it is preferable that the outside of a bottom surface of the microneedle patch can partially press a microneedle patch contained in other microneedle patch container. Generally, in order to supply hyaluronic acid and the medicinal ingredients by attaching the microneedle patch to face and to achieve a beauty effect, such as wrinkle removing, it is necessary that the microneedle patch is attached while repeating its attachment for a few days. Therefore, it is desirable in business that the number of sheets which is necessary for a series of use can be packaged all together.

It is preferable that a cut and a protrusion are provided in corresponding positions of the microneedle patch container and the lid to easily remove the lid from the container when the microneedle patch is used. This is because, although the microneedle patch container needs to be sealed from its manufacture until immediately before use, it needs to easily be taken out when the microneedle patch is used.

In the bottom surface of the microneedle patch container, a swollen part for easily picking the microneedle patch is preferably provided. This is because, even when the microneedle patch closely contacted to the container by the static electricity, the microneedle patch is made easier to be picked.

The surfaces of the microneedle patch container according to the present invention are preferably anti-static treated. This is because, when the container is charged electrostatically, the microneedle patch is attracted to the container and thus hardly taken out.

Although this microneedle patch container can hold the microneedles in a closed state, it cannot necessarily hold them in an aseptic state. To hold the microneedles in the aseptic state, it is desirable that after the container and the microneedles have been aseptic processed, the container is stored and sealed in a pouch formed with sterilized paper or a sterilized film sheet. A plastic sheet and an aluminum sheet can be preferably used as the sterilized film sheet. Since the aluminum sheet has high sealability, it is especially preferable.

In the case of a patch, that is, so-called an adhesive skin patch in which an active ingredient of an agent and an adhesive are mixed and spread on resin film, it is usual that a release sheet is put on the active ingredient, the release sheet is peeled off before attaching to skin, and the patch is attached to bring the active ingredient of the agent into contact with the skin directly. In this case, although the patch is desirably clean because it is attached on a stratum corneum of the skin, it is not required to be aseptic due to presence of barrier effect on the stratum corneum.

In this respect, conditions necessary for the microneedle patch container are severer than requirements necessary for a patch container. Since the microneedles are inserted into the skin, they must be hygienically preserved. Moreover, if the needles are not sharp, they cannot be inserted into the skin, so that hard matter which may damage a needle tip cannot be used. In addition, since the needles are inserted into the skin, matter about which it is doubtful whether or not it is safe in vivo, such as an adhesive agent, must not be attached. Namely, the microneedles must be held and preserved with only the release sheet portion in a sterile state and a state in which the microneedles are not brought into contact with any part of the container. Therefore, the microneedle patch container is inevitably different in structure from the patch container, and it cannot be designed on the analogy of the patch container.

In addition, when the microneedle array is flexible, a method for preserving a solid microneedle array cannot be used as it is. This is because holding methods are different between the solid microneedle array and the flexible microneedle array.

Resin which is easy in injection molding processing or press processing is preferable, but material of the microneedle patch container is not particularly limited. The microneedle patch container is especially preferably transparent or translucent because a situation of contents can be seen from the outside. Moreover, it is desirable that penetrability to air and vapor is low and that the microneedle patch can be stably protected for a long term. For example, polyethylene terephthalate (PET), polypropylene (PP) and polyethylene (PE) are preferable, among which PET is especially preferable because deterioration and stinking caused by sterilisation with gamma ray or electron beam irradiation are slight.

Advantageous Effects of Invention

According to the microneedle patch container of the present invention, the microneedle patch is held with the release sheet portion, and the microneedles portion does not contact with any part of the container. Even if the microneedle patch is a flexible sheet, it can be held hygienically until its unsealing. Using this container allows the microneedle patch to be easily taken out when needed. Furthermore, the containers may be stacked each other, and several microneedle patches which are necessary for a series of use may be simply packaged.

The microneedle patch container of the present invention is designed to avoid influence of static electricity. This is because, if the influence of the static electricity exists, the microneedle patch is attracted to the lid and popped up suddenly when the lid is removed, and the microneedle patch is attracted to the container and thus hardly taken out.

DESCRIPTION OF EMBODIMENTS

Hereinafter, the embodiments of the present invention will be described in accordance with examples. Although the present examples were designed to contain microneedle patches which had been designed on the assumption of being attached under an eye, the present invention is not limited to the shape of the examples, and the design may be suitably changed according to microneedle array patches with other shapes.

Figure 1:
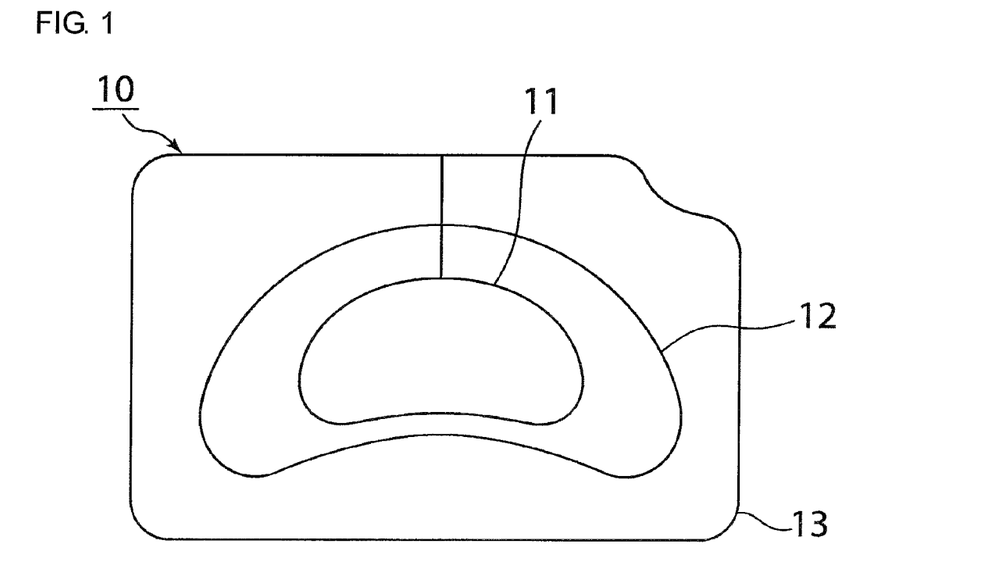
FIG. 1 shows a microneedle patch used in Example 1 to 3.

FIG. 1 shows a microneedle patch 10 used in the present examples. As shown in FIG. 1, a microneedle array 11 has a planar shape with a curved bottom of a semicylindrical cross section, a horizontal width of approximately 35 mm and a vertical width of approximately 15 mm. As an outline of the microneedle array 11 shown in FIG. 1, the semicylindrical cross section has a shape in which a convex curved part and another convex curved part, with a smaller curvature than the convex curved part, or another straight part are spaced from one another and in which ends of both parts are continued together. This shape is designed on the assumption of being attached under an eye. Microneedles of this microneedle array are provided on a flexible sheet to allow the entire microneedle array to change shape according to an unevenness of a face. The microneedle array comprises needles with a length of 30-1000 μm at the rate of 50-500 counts per cm$^2$, but the size of the microneedle is not limited, Although the main component is hyaluronic acid, the microneedles contain components which are effective for wrinkle removing of skin and activation of skin rejuvenation.

In about the same shape as the microneedle array portion, a large adhesive sheet 12 with a circumference of 2 to 10 mm is adhered to an opposite surface of the microneedle array surface. An adhesive surface is directed in the same direction as the array surface. Moreover, at the microneedle array surface side, a nearly rectangular release sheet 13 (70×45 mm) with the microneedle array portion removed is stuck to cover the adhesive surface. A bottom part of the adhesive sheet 12 is narrow to attach the microneedle array 11 as closely as possible to the eye.

Because a cutting line is provided in the centre of the release sheet 13, when the microneedle patch is used, an user has both ends of the release sheet and contacts the release sheet with an array-attached site (under the eye) expanding the form sheet to open, so that the microneedle patch is adhered by the adhesive sheet 12. Then, by tapping the microneedle array 11 surface, the microneedles are inserted into skin keratin. Since it is said that a point of skin which is sensitive to pain is inside by around 1 mm from a skin surface, the user feels little pain caused by this insertion.

EXAMPLE 1

Figure 2:
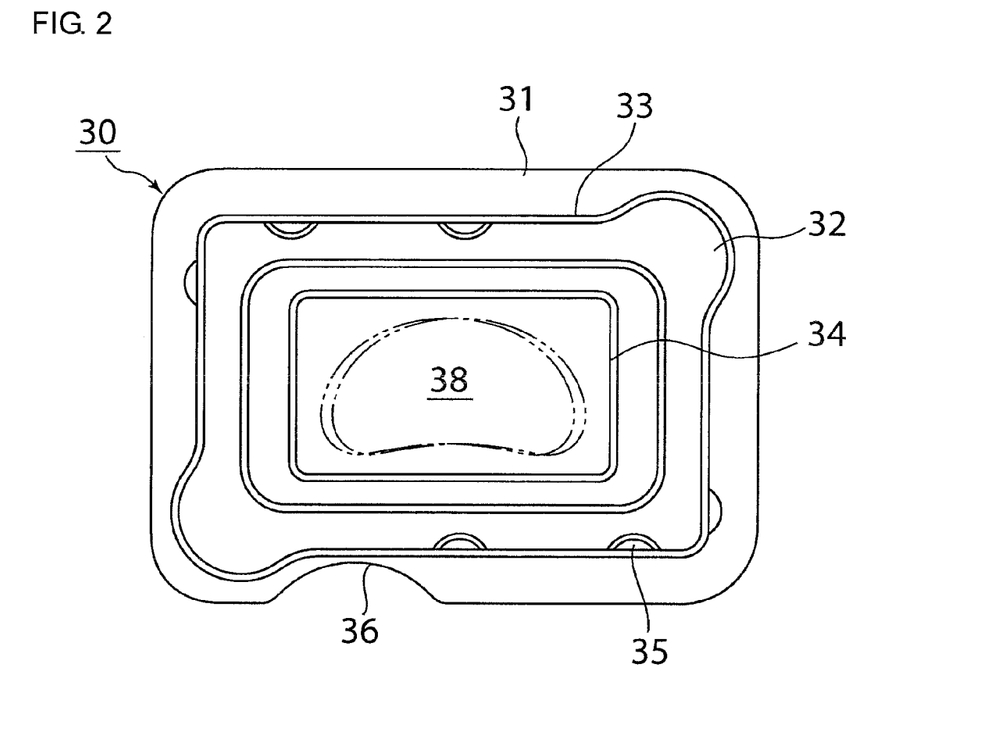
FIG. 2 shows the first example of the microneedle patch container.
Figure 3:
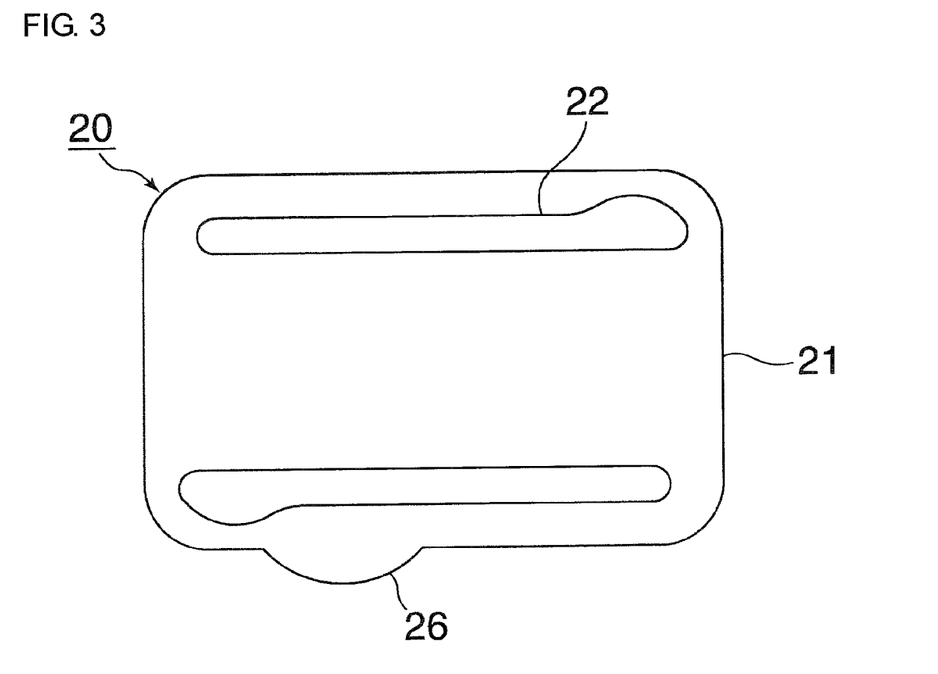
FIG. 3 shows a lid of the microneedle patch container of the first example.

FIG. 2 shows an example of a microneedle patch container suitable for the above-mentioned microneedle patch. It is made of polyethylene terephthalate (PET). A microneedle patch container 30 may be a container closed by covering with a lid. FIG. 3 shows an example of a lid 20. Surfaces of the microneedle patch container 30 and the lid 20 are anti-static treated.

The microneedle patch container 30 of the present example is an almost rectangular shape with outer dimensions of approximately 88×63 mm and has an almost rectangular bottom surface 32 with a depth of approximately 5 mm and a size of approximately 72×49 mm which is recessed from a peripheral portion 31 in the centre. The bottom surface 32 is a plane with an almost uniform depth and is continued to the peripheral portion 31 via a side surface 33. An almost oblong bottom-surface protruding portion 34 is provided from the bottom surface 32. A height of the bottom-surface protruding portion 34 is approximately 2 mm and an upper part of the bottom-surface protruding portion is curved. Four side surface convex parts 35 are provided inside the side surface 33 and a height of the side surface convex parts is the same as the bottom convex part 34.

The container 30 has a size in which the microneedle patch 10 fits precisely. The microneedle patch 10 is precisely stored inside the container by directing the microneedles 11 surface downward. A zone 38 shown by double two-dot chain lines in FIG. 2 shows a site at which the microneedles portion 11 exists when the microneedle patch 10 is contained in the container 30 and does not show structure of the container 30. Then, the microneedle patch 10 is supported by the bottom-surface protruding portion 34 and the side surface convex parts 35, and the microneedles portion 11 does not contact with any part of the container 30. Upper right and lower left swollen parts of the recess of the container in the figure are provided to pick the microneedle patch easily in taking the microneedle patch out of the container. Although the microneedle patch fits precisely in the container, it can be picked easily by inserting fingers into the swelling parts.

The lid 20 for the above-mentioned container is a rectangular shape with about the same size as the container 30. The lid 20 has recessed portions 22 which are recessed from a peripheral portion 21 and matched with the recess 32 of the container 30, When the container 30 is engaged with the lid 20, the microneedle patch is caught and held by these recessed portions 22 and by the bottom-surface protruding portion 34 and the side surface convex parts 35 of the container. A protrusion 26 is located outside the lid 30, and a cut 36 is located in a corresponding position outside the container 30. They are provided to easily remove the lid from the container.

In the microneedle patch container 30 of the present example, the microneedle patch is not completely pressed by the bottom-surface protruding portion 34 and the recessed portions 22 of the lid. If the microneedle patch is completely pressed, due to static electricity, the microneedle patch is attracted to the lid 20 and popped up suddenly when the lid is removed, and the microneedle patch is attracted to the container 30 and thus hardly taken out.

As shown in FIG. 2 and FIG. 3, the position of the bottom-surface protruding portion 34 of the container and the position of the recessed portions 22 of the lid shift from each other and are designed not completely to press the microneedle patch. In the present example, the recessed portions 22 of the lid are arranged towards a border of the bottom-surface protruding portion 34 from a top of the side surface convex parts 35. Moreover, the recessed portions 22 of the lid are provided in upper and lower areas of the figure, while they are not provided in right and left areas. Accordingly, the microneedle patch is not pressed down in right and left parts of the bottom-surface protruding portion 34 in FIG. 2. Providing the parts in which the microneedle patch is not pressed down to avoid influence of the static electricity allows the microneedle patch to be easily taken out.

It is possible that the microneedle patch container 30 of the present example is not covered with the lid and that other container is substituted for the lid to cover the microneedle patch container 30 from above with other container after the microneedle patches have been stored. Moreover, it is also possible that the microneedle patch container in which the microneedle patch has been stored is not covered with the lid and that it is contained, sealed and held in a pouch made of a sterile aluminum film sheet after aseptic process. Moreover, it is also possible that the microneedle patch container in which the microneedle patch has been stored is not covered with the lid, that it is instead covered with sterilized paper laminated with a heat-sealable film or polyethylene, and that the peripheral portion of the container and the film are fused by heat sealing to seal the microneedle patch container.

EXAMPLE 2

Figure 4:
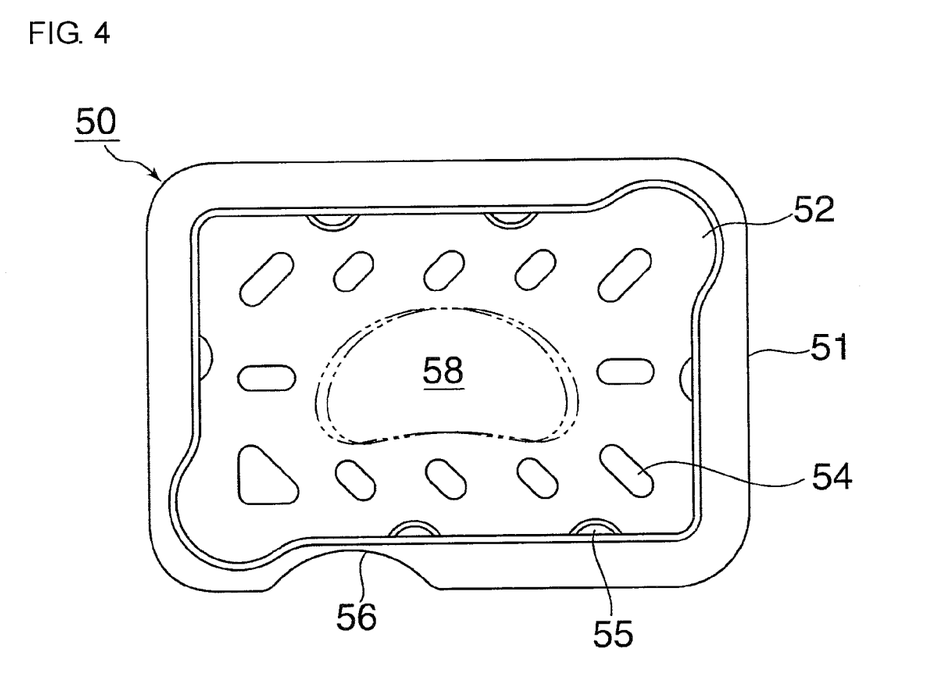
FIG. 4 shows the second example of the microneedle patch container.
Figure 5:
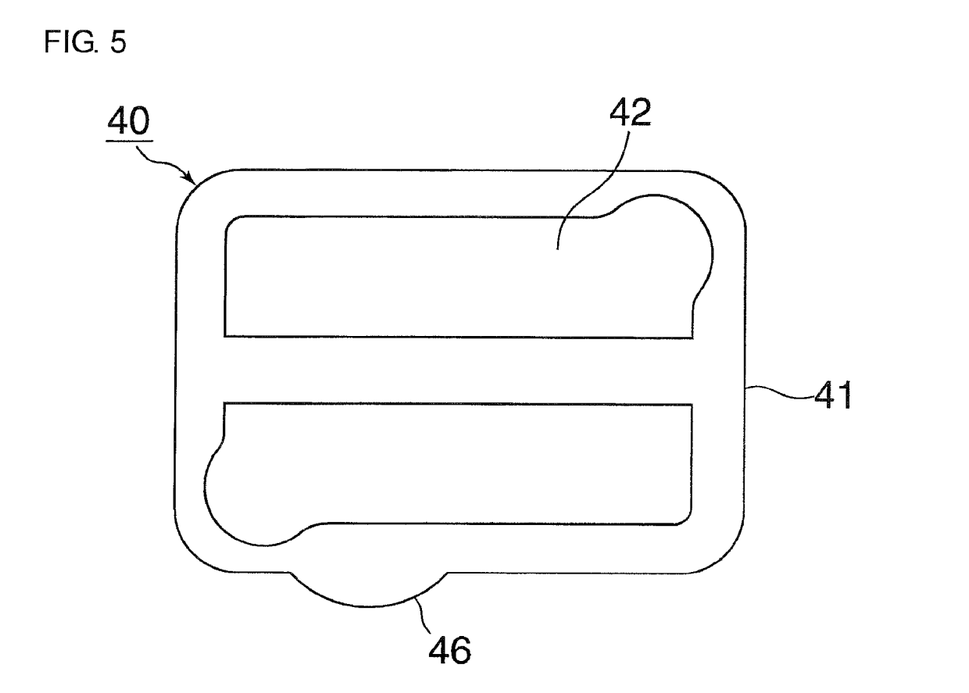
FIG. 5 shows a lid of the microneedle patch container of the second example.

FIG. 4 shows other example of the microneedle patch container. A microneedle patch container 50 may be a container closed by covering with a lid. FIG. 5 shows an example of a lid 40. The microneedle patch container 50 and the lid 40 are made of polyethylene terephthalate (PET) and their surfaces are anti-static treated.

The microneedle patch container 50 of the present example is an almost rectangular shape with outer dimensions of approximately 88×63 mm and has an almost rectangular bottom surface 52 with a depth of approximately 5 mm and a size of approximately 72×49 mm which is recessed from a peripheral portion 51 in the centre. The bottom surface 52 is a plane with an almost uniform depth and is continued to the peripheral portion 51 via a side surface 53. Twelve bottom-surface protruding portions 54 are provided from the bottom surface 52. Five of these in upper and lower areas of the figure are almost collinear, respectively. Upper parts of the bottom-surface protruding portions 54 are curved, and all of the bottom-surface protruding portions have the same height of approximately 2.5 mm.

Six side surface convex parts 55 are provided inside the side surface 53, and the inside of the side surface convex parts have a size in which the microneedle patch 10 fits just precisely. When the microneedle patch is contained in this container, the release sheet 13 is precisely fit inside the six side surface projections 55 not to move in the longitudinal and cross directions, and the bottom-surface protruding portions 54 support the release sheet 13 without contacting with the microneedle array 11. A zone 58 shown by double two-dot chain lines in FIG. 4 shows a site at which the microneedles portion 11 exists when the microneedle patch 10 is contained in the container 30 and does not show structure of the container 50. Then, the microneedle patch 10 is supported by the bottom-surface protruding portions 54 and the side surface convex parts 55, and the microneedles portion 11 does not contact with any part of the container 50.

The lid 40 for the container of the present example is a rectangular shape with about the same size as the container 50. The lid 40 has recessed portions 42 which are recessed from a peripheral portion 41 and matched with the recess of the container. When the container 50 is engaged with the lid 40, the recessed portions 42 correspond to the bottom-surface protruding portions 54 of the container to hold the entire microneedle patch 10 from above and below. A protrusion 46 is located outside the lid 40, and a cut 56 is located in a corresponding position outside the container 50. They are provided to easily remove the lid from the container.

Unlike the case of Example 1, in the microneedle patch container of the present example, a position where the microneedle patch container 50 and the lid 40 are closely contacted is only on the side surface projections. Accordingly, the microneedle patch is not strongly pressed but caught between the bottom-surface protruding portions of the container and the recessed portions of the lid with a little allowance. Moreover, the recessed portions of the lid are provided in upper and lower areas of the figure, while they are not provided in right and left areas. The microneedle patch is placed on the bottom-surface protruding portions in right and left areas of FIG. 4, where it is not sandwiched from above.

EXAMPLE 3

Figure 6:
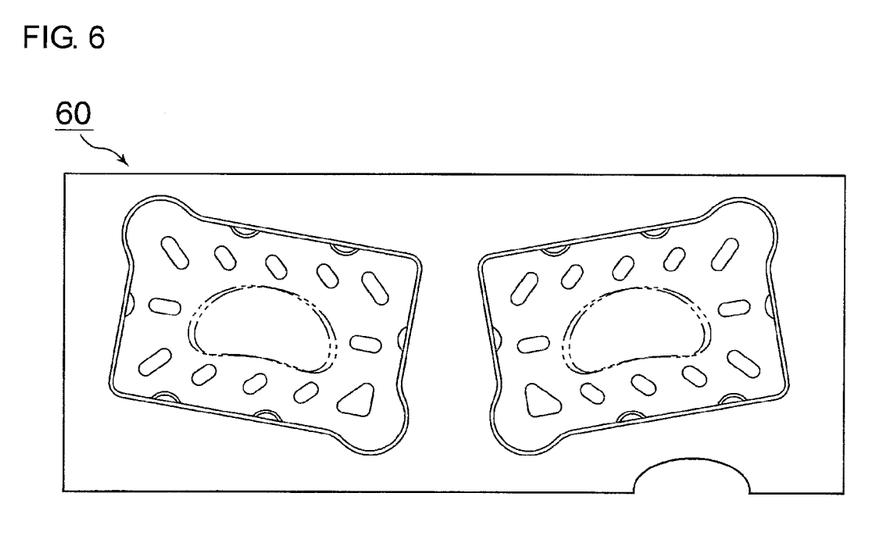
FIG. 6 shows the third example of the microneedle patch container.

FIG. 6 shows an example of a microneedle patch container which can contain two microneedle patches. A microneedle patch container 60 may be a container closed by covering with a lid. The microneedle patch container 60 is made of polyethylene terephthalate (PET) and its surface is anti-static treated.

Although the microneedle patch container 60 has two bottom parts provided in a peripheral portion, configuration of each bottom part is similar to that of the container 50, so that further detail is omitted. Moreover, it is considered that the lid of the container 60 can be easily estimated based on FIG. 6 and the lid 40, so that its illustration is omitted. The microneedle patches are held like the case of Example 2.

EXAMPLE 4

Figure 7:
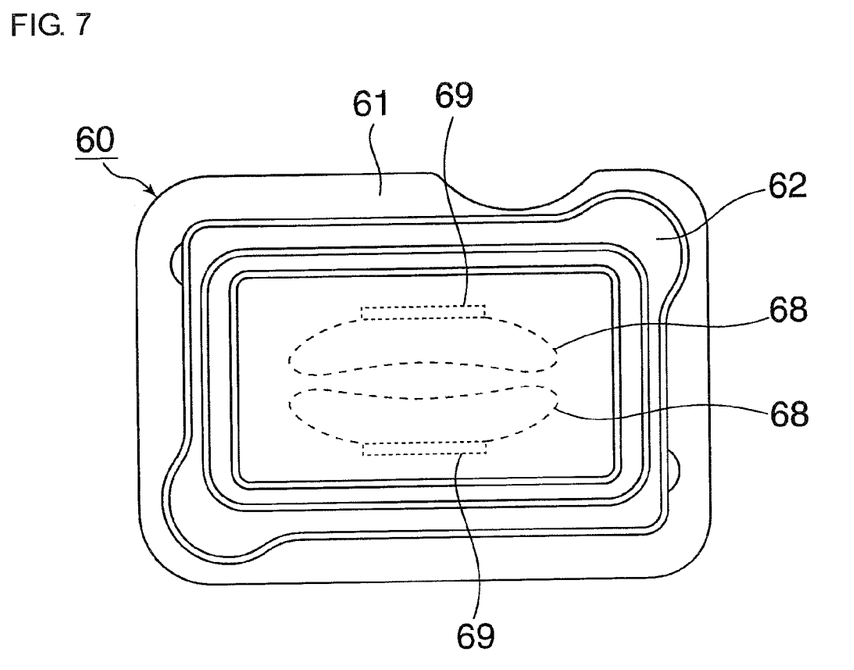
FIG. 7 shows the fourth example of the microneedle patch container.
Figure 8:
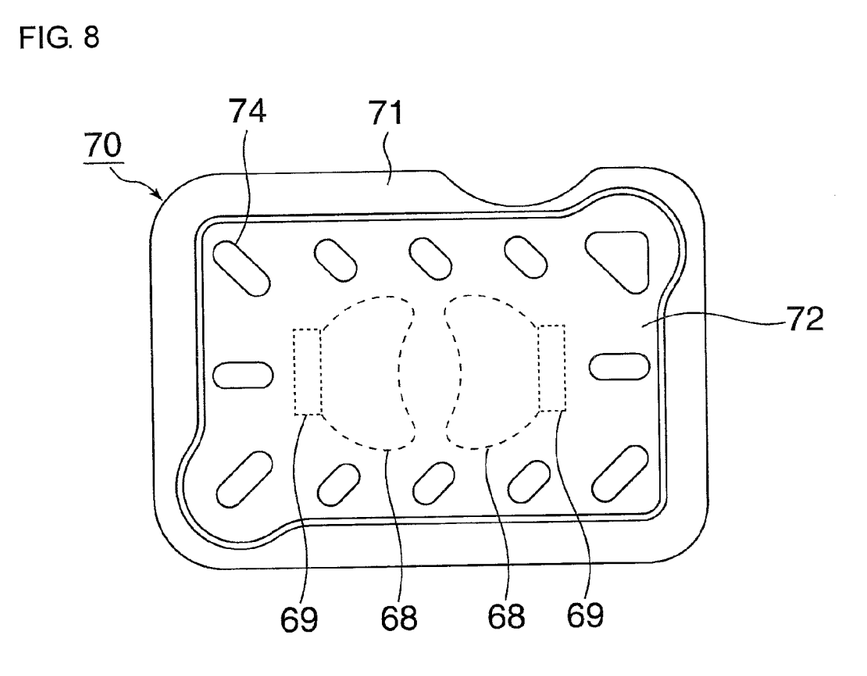
FIG. 8 also shows the fourth example of the microneedle patch container.

FIG. 7 and FIG. 8 show examples of a microneedle patch container in which a microneedle patch holding two microneedle arrays can be contained. In the microneedle patch, the two microneedle arrays 68 are held on one piece of release sheet paper. Moreover, in the case of the present example, adhesive tapes 69 are attached to only a part of the microneedle arrays. By this means, the two microneedle arrays can be easily contained than the case of FIG. 6.

FIG. 7 shows the microneedle patch container 60 holding two elongate microneedle arrays. Outer dimensions are slightly bigger than the case of FIG. 2. A bottom surface 62 with a depth of approximately 5 mm recessed from a peripheral portion 61 is provided in the centre. An almost oblong bottom-surface protruding portion 64 is provided from the bottom surface. The bottom-surface protruding portion 64 may be formed relatively larger than the bottom-surface protruding portion 34 of FIG. 2 to contain the two microneedle arrays. Moreover, a lateral bottom-surface protruding portion may be added between the two microneedle arrays of a central part. Configurations of other parts are similar to FIG. 2, so that their description is omitted.

An example of the microneedle arrays 68 and an example of the adhesive tape 69 are shown by broken lines in FIG. 7. These broken lines are illustrations when the microneedle patch is contained in the container, and they do not show structure of the container.

FIG. 8 shows the microneedle patch container 70 holding two thick microneedle arrays. Outer dimensions are slightly bigger than the case of FIG. 4. A nearly rectangular bottom surface 72 with a depth of approximately 5 mm recessed from a peripheral portion 71 is provided in the centre. The bottom surface 72 is a plane with an almost uniform depth and is continued to the peripheral portion 71 via a side surface. Twelve bottom-surface protruding portions 74 are provided from the bottom surface 72. Five of these in upper and lower areas of the figure are almost collinear, respectively. Upper parts of the bottom-surface protruding portions 74 are curved, and all of the bottom-surface protruding portions have the same height of approximately 2.5 mm. Compared to FIG. 4, the bottom-surface protruding portion 74 of FIG. 8 spreads relative to the entire container than the bottom-surface protruding portion 54 of FIG. 4, to hold the two microneedle arrays. This is because two microneedle arrays are held in a narrow space.

An example of the microneedle arrays 68 and an example of the adhesive tape 69 are shown by broken lines in FIG. 8. These broken lines are illustrations when the microneedle patch is contained in the container, and they do not show structure of the container.

EXAMPLE 5

Figure 9:
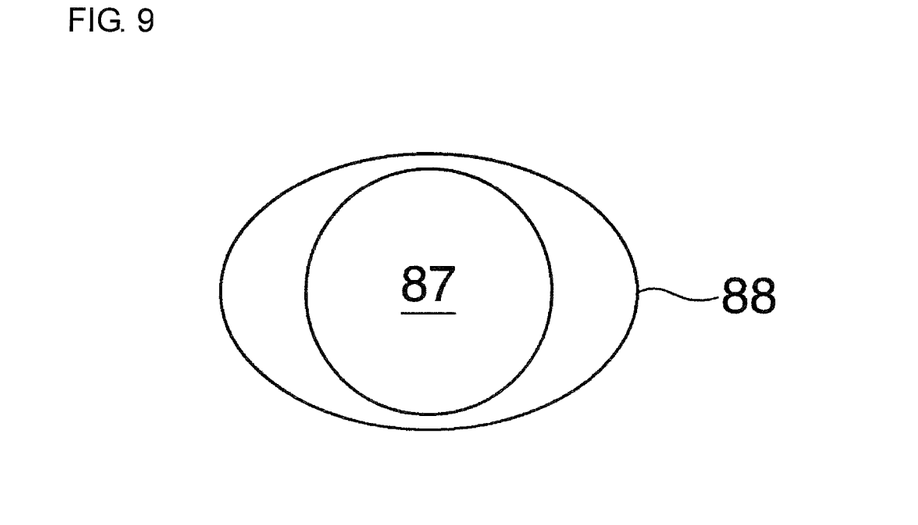
FIG. 9 shows a microneedle array used in Example 5.

An example for containing four microneedle arrays in one microneedle patch container is shown. FIG. 9 shows a microneedle array with an adhesive sheet provided only in a peripheral portion of the microneedle array. The microneedle array comprises the adhesive sheet of course on a surface side where microneedles of the microneedle array are not provided, and it is convenient that the adhesive sheet does not exist on the backside of a part where the microneedles exist. Such a microneedle patch holding four microneedle arrays on one piece of release sheet is convenient when the four microneedle patches are used at a time.

Figure 10:
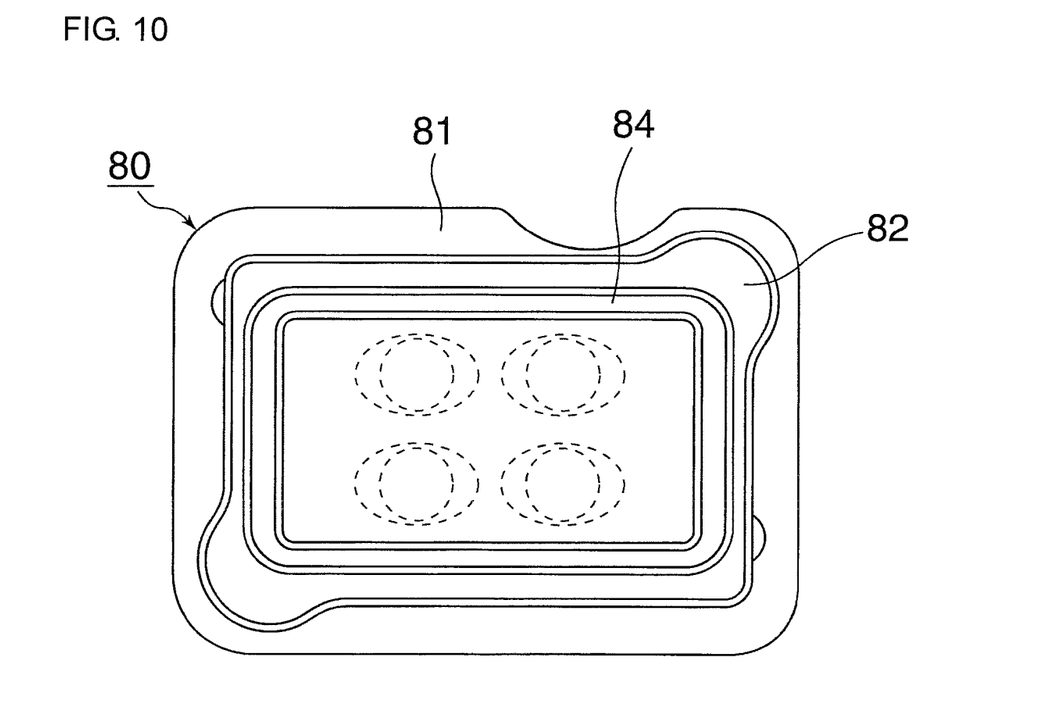
FIG. 10 shows the fifth example of the microneedle patch container.

Although a microneedle patch container 80 of Example 5 may be the same shape as that of Example 4 as shown in FIG. 10, a container which is larger as a whole is easy to use for containing the four microneedle arrays. A bottom surface 82 with a depth of approximately 5 mm recessed from a peripheral portion 81 is provided in the centre. An almost oblong bottom-surface protruding portion 84 is provided from the bottom surface. It is convenient that the bottom-surface protruding portion 84 is formed relatively larger than the bottom-surface protruding portion 34 of FIG. 2 to contain the four microneedle arrays. Moreover, a cross or columnar bottom-surface protruding portion may be added between the four microneedle arrays of a central part. Configurations of other parts are similar to FIG. 2, so that their description is omitted.

The four microneedle arrays shown in FIG. 9 are shown by broken lines in FIG. 10. These broken lines are illustrations when the microneedle patch is contained in the container, and they do not show structure of the container.

REFERENCE NUMERALS 10 microneedle patch
11 microneedle array
12 adhesive sheet
13 release sheet
20, 40 lid for microneedle patch container
21, 41 peripheral portion of lid
22, 42 recess part of lid
26, 46 protrusion for to release fitting between lid and container
30, 50 microneedle patch container
31, 52, 61, 71, 81 peripheral portion of container
32, 52, 62, 72, 82 bottom surface recessed from peripheral portion of container
34, 54, 64, 74, 84 bottom surface convex part provided in recess of bottom surface
35, 55 side surface convex part
38, 58 zone 60, 70 microneedle patch container which can contain two microneedle arrays
68 microneedle array
69 adhesive tape
80 microneedle patch container which can contain four microneedle arrays
87 microneedle array
88 microneedle patch

The invention claimed is:

1. A microneedle patch container having a flexible microneedle patch therein, said container comprising:
    one or plural bottom surfaces recessed from a peripheral portion;
    a side surface continuously connecting the one or plural bottom surfaces with the peripheral portion; and
    a bottom-surface protruding portion projecting from each of the one or plural bottom surfaces,
    wherein the flexible microneedle patch comprises an adhesive sheet having an adhesive surface, a microneedle array disposed on the adhesive surface, and a release sheet portion stuck on the adhesive surface outside a region wherein the microneedle array is disposed, and
    wherein the release sheet portion of the flexible microneedle patch is held with the bottom-surface protruding portion of each of the one or plural bottom surfaces so that a microneedle of the microneedle array is elongated from the adhesive surface towards the one or plural bottom surfaces of the microneedle patch container.

2. The microneedle patch container according to claim 1, further comprising a lid, wherein
    the lid has recessed portions which respectively press the flexible microneedle patch on each bottom-surface protruding portion in a position corresponding to a part, but not all, of the bottom-surface protruding portion.

3. The microneedle patch container according to claim 2, characterized in that an area of each bottom-surface protruding portion of the container is larger than an area of the respective recessed portion of the lid.

4. The microneedle patch container according to claim 2, characterized by comprising a cut and a protrusion in corresponding positions of the microneedle patch container and the lid.

5. The microneedle patch container according to claim 1, characterized in that each bottom-surface protruding portion has a rectangular shape.

6. The microneedle patch container according to claim 1, characterized in that each bottom-surface protruding portion is arranged so that a plurality of convex parts support four sides of the release sheet portion of the flexible microneedle patch.

7. The microneedle patch container according to claim 1, wherein the flexible microneedle patch holds two or more microneedle arrays.

8. A plurality of microneedle patch containers, comprising:
    first and second microneedle patch containers, each of said first and second microneedle patch containers corn rising the microneedle patch container having the flexible microneedle patch therein according to claim 1,
    wherein the first and second microneedle patch containers are stacked such that the release sheet portion of the flexible microneedle patch in the first microneedle patch container is partially pressed by a bottom part of the second microneedle patch container.

9. The microneedle patch container according to claim 1, characterized in that a swollen part for accommodating fingers of a user and facilitating easy pick up of the flexible microneedle patch is provided in the bottom surface.

10. The microneedle patch container according to claim 1, characterized in that the surfaces are anti-static treated.

11. The microneedle patch container according to claim 1, characterized in that the peripheral portion of the container is fused and sealed by heat sealing with a heat-sealable film or with the film and paper laminated with the film.

* * * * *